US00PP19559P2

(12) United States Plant Patent
van Paemel

(10) Patent No.: US PP19,559 P2
(45) Date of Patent: Dec. 9, 2008

(54) ***HELLEBORUS* PLANT NAMED 'SNOW LOVE'**

(50) Latin Name: *Helleborus ×nigercors*
Varietal Denomination: Snow Love

(75) Inventor: Thierry van Paemel, Oostkamp (BE)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 11/978,496

(22) Filed: Oct. 29, 2007

(51) Int. Cl.
*A01H 5/00* (2006.01)

(52) U.S. Cl. ..... Plt./439

(58) Field of Classification Search ..... Plt./439
See application file for complete search history.

*Primary Examiner*—Kent L Bell
(74) *Attorney, Agent, or Firm*—C. A. Whealy

(57) ABSTRACT

A new and distinct cultivar of *Helleborus* plant named 'Snow Love', characterized by its upright and mounded plant habit; strong and moderately vigorous growth habit; numerous light green-colored flowers; long flowering period; and good garden performance.

2 Drawing Sheets

Botanical designation: *Helleborus×nigercors.*

Cultivar denomination: 'SNOW LOVE'.

BACKGROUND OF THE INVENTION

The present invention relates to a new and distinct cultivar of *Helleborus,* botanically known as *Helleborus×nigercors* and hereinafter referred to by the name 'Snow Love'.

The new *Helleborus* originated from a cross-pollination in Oostkamp, Belgium, of a proprietary selection of *Helleborus niger* designated as Wilgenbroek Selection, not patented, as the female, or seed, parent with a proprietary selection of *Helleborus×sternii,* also designated as Wilgenbroek Selection, not patented, as the male, or pollen, parent. The new *Helleborus* was discovered and selected by the Inventor as a single flowering plant from within the progeny of the stated cross-pollination grown in a controlled environment in Oostkamp, Belgium in 2005.

Asexual reproduction of the new *Helleborus* by vegetative cuttings in a controlled environment in Zandevoort, The Netherlands since 2005, has shown that the unique features of this new *Helleborus* are stable and reproduced true to type in successive generations.

SUMMARY OF THE INVENTION

The cultivar Snow Love has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Snow Love'. These characteristics in combination distinguish 'Snow Love' as a new and distinct cultivar of *Helleborus:*

1. Upright and mounded plant habit.
2. Strong and moderately vigorous growth habit.
3. Numerous light green-colored flowers.
4. Long flowering period.
5. Good garden performance.

Plants of the new *Helleborus* can be compared to plants of the parent selections. Plants of the new *Helleborus* are more freely flowering than plants of the parent selections and also differ in flower color.

Plants of the new *Helleborus* can be compared to plants of the *Helleborus×nigercors* cultivar White Beauty, not patented. Plants of the new *Helleborus* differ primarily from plants of the cultivar White Beauty in the following characteristics:

1. Plants of the new *Helleborus* are more upright than plants of the cultivar White Beauty.
2. Plants of the new *Helleborus* are more freely flowering than plants of the cultivar White Beauty.
3. Plants of the new *Helleborus* flower for a longer period of time than plants of the cultivar White Beauty.
4. Plants of the new *Helleborus* and the cultivar White Beauty differ in flower color as plants of the cultivar White Beauty have creamy white-colored flowers.

BRIEF DESCRIPTION OF THE PHOTOGRAPHS

The accompanying colored photographs illustrate the overall appearance of the new *Helleborus,* showing the colors as true as it is reasonably possible to obtain in colored reproductions of this type. Colors in the photographs may differ slightly from the color values cited in the detailed botanical description which accurately describe the colors of the new *Helleborus.*

The photograph at the top of the first sheet comprises a side perspective view of a typical flowering plant of 'Snow Love' grown in a container.

The photograph at the bottom of the first sheet is a close up view of a typical leaf of 'Snow Love'.

The photograph on the second sheet is a close-up view of a typical flower of 'Snow Love'.

DETAILED BOTANICAL DESCRIPTION

The aforementioned photographs and following observations, measurements and values describe plants grown in Oostkamp, Belgium in containers during the winter in an outdoor nursery and under conditions which closely approximate commercial *Helleborus* production. During the production of the plants, day temperatures ranged from about 4° C. to about 15° C. and night temperatures ranged from about −1° C. to about 8° C. Plants were about one year old when the photographs and the description were taken. In the description, color references are made to The Royal Horticultural Society Colour Chart, 2001 Edition, except where general terms of ordinary dictionary significance are used.

Botanical Classification: *Helleborus×nigercors* cultivar Snow Love.

Parentage:

*Female, or seed, parent.*—Proprietary selection of *Helleborus niger* designated as Wilgenbroek Selection, not patented.

*Male, or pollen, parent.*—Proprietary selection of *Helleborus×sternii* designated as Wilgenbroek Selection, not patented.

Propagation:

*Type.*—By vegetative cuttings.

*Time to initiate.*—About three weeks at 20° C.

*Time to develop roots.*—About six weeks at 20° C.

*Root description.*—Thick, fleshy, fibrous.

Plant description:

*Plant form and growth habit.*—Herbaceous perennial. Upright and mounded plant habit; flattened globular. Strong and moderately vigorous growth habit. Leaves and flowering stems developing from the plant base. About ten leaves per basal rosette.

*Plant height.*—About 28.7 cm.

*Plant diameter* (*area of spread*).—About 32.8 cm.

Foliage description:

*Arrangement.*—Palmately compound with five leaflets per leaf.

*Leaf length.*—About 17.1 cm.

*Leaf width.*—About 18.4 cm.

*Terminal leaflet lengthy.*—About 11.7 cm.

*Terminal leaflet width.*—About 4.8 cm.

*Lateral leaflet length.*—About 9.7 cm.

*Lateral leaflet width.*—About 4 cm.

*Leaflet shape.*—Narrowly elliptic to obovate.

*Leaflet apex.*—Acute.

*Leaflet base.*—Attenuate.

*Leaflet margin.*—Serrate.

*Leaflet texture, upper and lower surfaces.*—Smooth, glabrous; leathery.

*Leaflet venation pattern.*—Pinnate.

*Leaflet color.*—Developing foliage, upper surface: 137A. Developing foliage, lower surface: 146A. Mature foliage, upper surface: Darker than between 139A and 147A; venation, 144A to 144B. Mature foliage, lower surface: 147B; venation, 183B.

Petiole. —Length: About 15.7 cm. Diameter: About 5 mm. Texture, upper and lower surfaces: Smooth, glabrous. Color, upper and lower surfaces: 144A tinged with 187B.

Flower description:

*Flower arrangement and shape.*—Single rotate flowers arranged on panicles; flowers face outwardly to nodding. Freely flowering habit, about 14 flowers develop per inflorescence. Petals not observed.

*Fragrance.*—None detected.

*Natural flowering season.*—Long flowering period; plants flower from December through April in Belgium.

*Flower longevity on the plant.*—About ten days; flowers not persistent.

*Flower buds.*—Length: About 2.6 cm. Diameter: About 1.4 cm. Shape: Ovoid. Color: 145A to 145C; venation, 178A to 178B.

*Inflorescence size.*—Length: About 27.8 cm. Diameter: About 22.4 cm.

*Flowers.*—Diameter: About 8.4 cm. Depth (height): About 2.6 cm.

*Sepals.*—Arrangement: Five in a single whorl. Length: About 4.1 cm. Width: About 3.5 cm. Shape: Ovate to broadly elliptic. Apex: Obtuse. Base: Attenuate. Margin: Entire. Texture, upper and lower surfaces: Smooth, glabrous. Color: When opening, upper surface: 145D; towards the base, 144B. When opening, lower surface: 145C; towards the base, 145A to 145B. Fully opened, upper surface: 145D; towards the base, 144B; with development, color becoming closer to 143B to 143C, margins, N144A. Fully opened, lower surface: 145B to 145C; towards the base, 145A; with development, color becoming closer to 146C, venation, 176B.

*Peduncles.*—Strength: Moderately strong. Length: About 19.8 cm. Diameter: About 1 cm. Aspect: About 15° from vertical. Texture: Smooth, glabrous. Color: 144A heavily overlain with 187B.

*Pedicels.*—Strength: Moderately strong. Length: About 4.4 cm. Diameter: About 2.5 mm. Aspect: About 20° from vertical. Texture: Smooth, glabrous. Color: 145A.

*Reproductive organs.*—Stamens: Quantity per flower: About 70. Filament length: About 1.8 cm. Filament color: 155B. Anther shape: Reniform. Anther length: About 2 mm. Anther color: 4A. Pollen amount: Scarce. Pollen color: 4C. Pistils: Quantity per flower: About five. Pistil length: About 1.1 cm. Stigma shape: Club-shaped. Stigma color: 150D. Style length: About 1 cm. Style color: 145C to 145D. Ovary color: 144B to 144C. Nectaries: Arrangement: About 13 subtending the filaments. Length: About 7 mm. Diameter, at apex: About 3 mm. Diameter, at base: About 1 mm. Color: 144A; towards the apex, N144A.

*Seeds/fruits.*—Seed and fruit development has not been observed.

Garden performance: Plants of the new *Helleborus* have been observed to have good garden performance and to tolerate rain, wind and temperatures from about −20° C. to about 30° C.

Pathogen/pest resistance: Plants of the new *Helleborus* have not been shown to be resistant to pathogens and pests common to *Helleborus*.

It is claimed:

1. A new and distinct *Helleborus* plant named 'Snow Love' as illustrated and described.

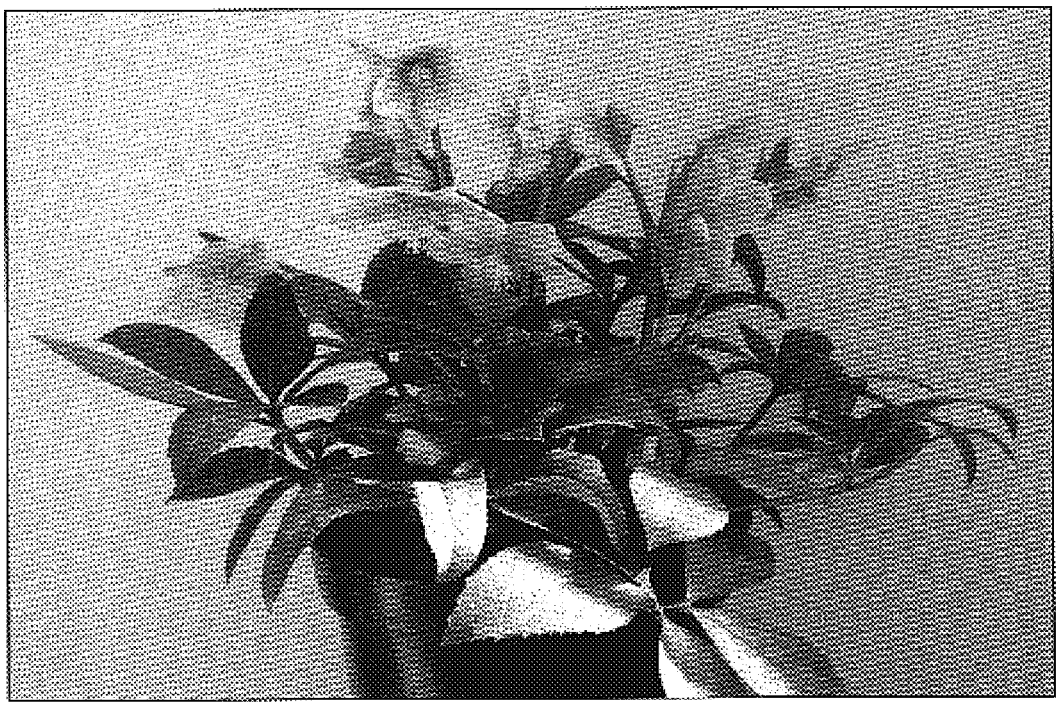
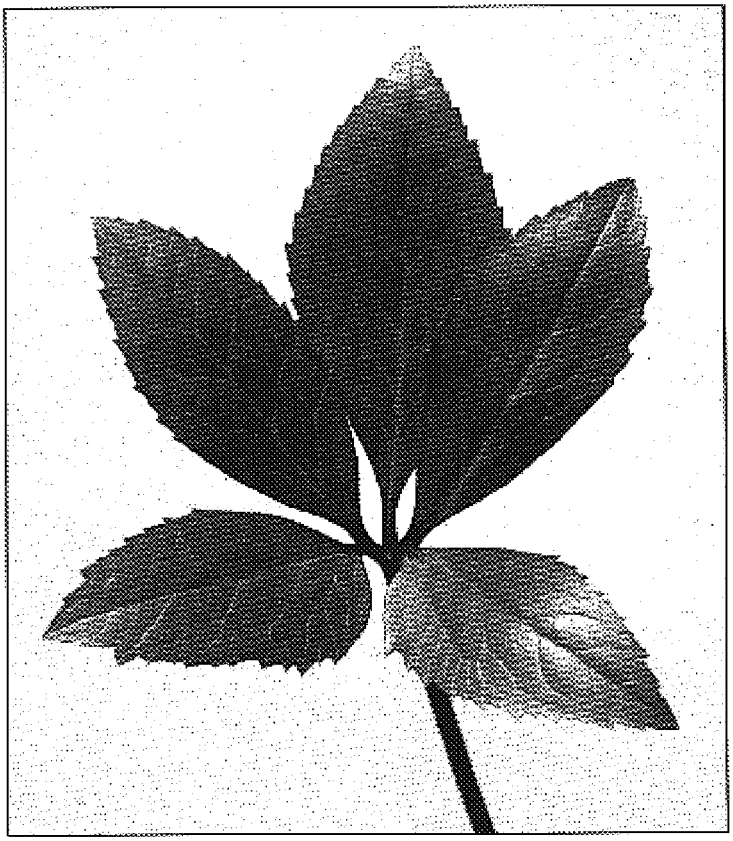

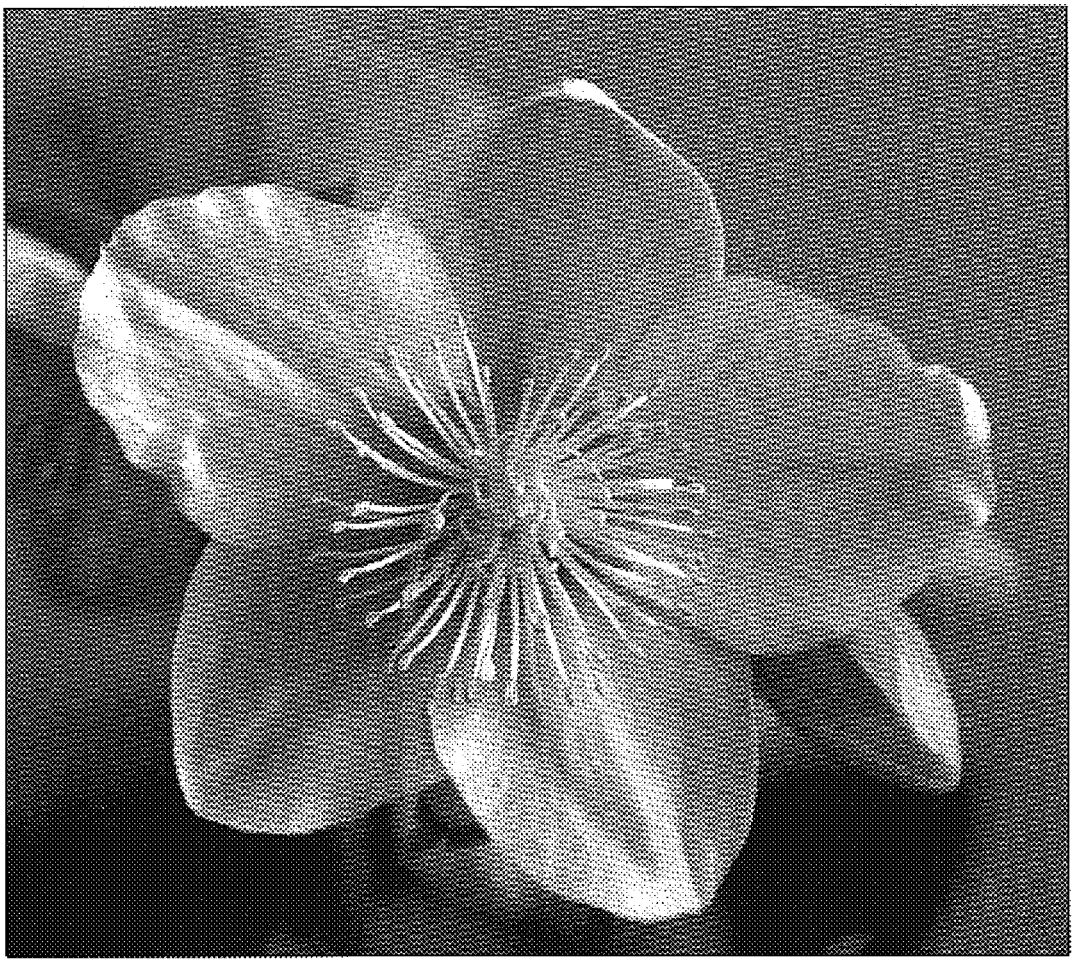

* * * * *